United States Patent [19]  [11] 4,270,924
Crooke et al.  [45] Jun. 2, 1981

[54] DIAGNOSTIC METHOD FOR DETECTING CANCER

[76] Inventors: Stanley T. Crooke, 110 Scottholm Blvd., Syracuse, N.Y. 13224; Louis Galvan, 6211 Pincay Oaks Dr., Houston, Tex. 77088

[21] Appl. No.: 124,961

[22] Filed: Mar. 13, 1980

Related U.S. Application Data

[63] Continuation-in-part of Ser. No. 28,732, Apr. 10, 1979, abandoned.

[51] Int. Cl.³ .................... G01N 33/54; G01N 33/68
[52] U.S. Cl. .................................. 23/230 B; 23/902; 23/915
[58] Field of Search .................. 23/230 B, 902, 915; 424/12

[56] References Cited

PUBLICATIONS

Galvan, The Pharmacologists (Abs.) 20(3): 238 (1978), "Inhibition of PM-2 DNA Breakage by a Human Serum Protein."
Lewis et al., FEBS Letters, vol. 92, No. 2, Aug. 1978, 211-213, "A Serum DNA-Binding Protein Absent in Malignant Diseases."
Parsons et al., Europ. J. Biochem. 71:1-8 (1976), "Purification and Identification of a Human-Serum DNA—Binding Protein Associated with Malignant Diseases."
Roberts et al., Amer. J. Med. 65:437-445, (1978), "Identification of Antinative DNA Antibodies in Cryoglobulinemic."

Primary Examiner—Arnold Turk
Attorney, Agent, or Firm—David M. Morse

[57] ABSTRACT

Diagnostic method for detecting cancer in humans comprising assaying a serum sample for concentration of a particular DNA-binding protein. The concentration of this serum protein has been found to be significantly different in patients having cancer than in cancer-free patients.

3 Claims, No Drawings

DIAGNOSTIC METHOD FOR DETECTING CANCER

The Government has rights in this invention pursuant to cancer research grant CA-10893 awarded by the National Cancer Institute of the Department of Health, Education and Welfare.

CROSS-REFERENCE TO RELATED APPLICATION

This application is a continuation-in-part application of our prior, co-pending application Ser. No. 28,732 filed Apr. 10, 1979 and now abandoned.

BACKGROUND OF THE INVENTION

1. Field of the Invention

This invention relates to a diagnostic test method for detecting malignant neoplasms.

2. Description of the Prior Art

New methods for the detection of cancer are clearly needed. In many cases early diagnosis of cancer would greatly improve chances for effecting a complete remission of the disease.

The literature describes previous attempts to demonstrate the presence of tumor-specific components such as hormones and antigens in the blood of cancer patients. Such attempts have been largely unsuccessful, however, and a practical, noninvasive diagnostic procedure based on the level of a tumor-specific serum component has remained up to now an elusive goal.

Recently DNA-binding proteins have been found in serum of patients with neoplasias, systemic lupus erythematosus and other inflammatory disorders [see, for example, *FEBS Letters* 92(2):211–213 (1978); *Europ. J. Biochem.* 71:1–8 (1976); *Amer. J. Med.* 65:437–445 (1978)]. No provision of a suitable assay procedure for such serum proteins has been made, however, which would be necessary for a practical diagnostic method. Moreover, the serum proteins previously described do not appear to show the degree of selectivity desired in a cancer screening method.

The inhibitor serum protein utilized in the present invention is disclosed in *The Pharmacologists* (Abs.) 20(3):238 (1978). The abstract, however, gives no indication that the protein is present at different levels in patients having cancer than in cancer-free patients.

SUMMARY OF THE INVENTION

The present invention provides a generally applicable diagnostic test method for detecting malignant neoplasms in humans. More particularly, the invention provides a diagnostic method for indicating the existence of malignant neoplasms by assaying human serum samples for the presence of a specific DNA-binding protein. The method is useful for the early detection of malignant disease and as an indicator of disease progression in a cancer patient undergoing treatment.

The present method is based on the discovery that a certain DNA-binding protein (hereinafter referred to as inhibitor protein X) is present in significantly reduced concentrations in the serum of patients with cancer than in cancer-free patients. By providing a sensitive assay for this serum protein, the present invention mades possible a rapid, noninvasive and accurate method for detecting the existence of cancer.

DETAILED DESCRIPTION OF THE INVENTION

The presence of a particular DNA-binding protein in human serum was discovered by the present inventors during investigation of the bleomycin-induced degradation of PM-2 DNA (Pseudomonas bacteriophage covalently closed circular DNA). Observation of the inhibition of this degradation by human serum led to studies on the nature of the inhibition and attempts to identify the inhibitor compound.

The inventor's hypothesis that inhibition of the PM-2 DNA degradation reaction was due to a serum protein was confirmed when treatment with pronase resulted in the loss of inhibitory activity. Treatment with DNAase I or pancreatic RNAase had no effect on the inhibitory activity of the serum. Sera from dogs and calves were not inhibitory, nor were human albumin and immunoglobulins.

The inhibitor protein was purified under non-denaturing conditions by the use of molecular filters, dialysis and Sephadex column chromatography. Purification of the protein was increased considerably by binding the protein to DNA, isolating the DNA-protein complex from the unbound protein and then dissociating the protein from the DNA by treatment with urea. Purification by SDS-polyacrylamide gel electrophoresis and isoelectric focusing is estimated to result in a greater than 2000-fold purification. Isoelectric focusing gel electrophoresis indicates that the inhibitor is a protein having a molecular weight of approximately 64,000 daltons and a pI of 5.9. This protein has been tentatively designated herein as inhibitor protein X.

Inhibitor protein X exerts its inhibitory effect by binding to the DNA. DNA-binding has been demonstrated by agarose gel electrophoresis, isolation of the DNA-protein complex, fluoroescence quenching and circular dichroism studies.

In investigating the nature of inhibitor protein X, it was found quite unexpectedly that there was a significant difference in the level of this protein in the serum of patients having cancer than in serum of cancer-free patients. Based on this important discovery, the present inventors sought a sensitive and rapid assay for the presence of inhibitor protein X in human serum.

PM-2 DNA has been previously employed in a spectrophotofluorometric assay to determine bleomycin biochemical activity [*Cancer Res.* 38:3322–3326 (1978)]. The mechanism of action of bleomycin appears to be related to its ability to degrade DNA, and the decrease in binding of ethidium bromide (2,7-diamino-10-ethyl-9-phenyl-phenanthridinium bromide) to PM-2 DNA induced by bleomycin as determined by fluorescence spectrometry can thus be used to assay for bleomycin activity.

As noted above inhibitor protein X has been found to act as an inhibitor of bleomycin-induced degradation of PM-2 DNA. In view of this the fluorometric assay previously used to measure bleomycin activity may also be used to assay for the concentration of inhibitor protein X in human serum. The level of inhibitor protein X can then be employed to predict the likelihood of cancer in the patient being screened.

The present invention thus provides a method for detecting cancer in humans which comprises the steps of:

(a) obtaining a blood sample from a patient to be screened for cancer;

(b) determining the concentration of inhibitor protein X in said sample; and (c) comparing said concentration as determined in step (b) with the norm inhibitor protein X concentration associated with serum of cancer-free patients, whereby a significant reduction of inhibitor protein X concentration relative to the norm concentration indicates the probability of cancer.

The particular assay procedure used in step (b) to determine the serum inhibitor protein X concentration is not critical, and the invention in its broadest aspect lies in the finding that the inhibitor protein X concentration (however determined) can be used as a diagnostic tool for a wide variety of human cancers.

One assay procedure which has been found advantageous is the PM-2 DNA fluorescence assay described in *Cancer Res.* 38:3322–3326 (1976). Use of this assay is based on the inhibitory effect of inhibitor protein X on the well-known bleomycin-induced degradation of PM-2 DNA reaction. When this assay is employed, it is convenient to express the inhibitor protein X concentration as an $IC_{50}$ value wherein $IC_{50}$ is defined as the concentration of inhibitor protein X required to inhibit 50% of bleomycin-induced degradation of PM-2 DNA. This $IC_{50}$ value may then be compared to the norm $IC_{50}$ value associated with serum of cancer-free patients, and a significant elevation of the $IC_{50}$ value from the norm value will indicate the probability of cancer.

Details of the PM-2 DNA fluorescence assay for inhibitor protein X are as follows:

A mixture is first prepared of a serum sample (e.g. a 50 $\mu$l sample) from a patient to be screened with a solution of bleomycin, PM-2 DNA and 2-mercaptoethanol in pH 9.5 buffer. Typically a 50 $\mu$l serum sample is mixed with 450 $\mu$l of a solution comprising 35 nM bleomycin, 8.3 $\mu$M PM-2 DNA and 25 mM 2-mercaptoethanol in pH 9.5 sodium borate buffer (0.015 M NaCl: 0.05 M sodium borate).

The above mixture is then incubated at 37° C. for 30 minutes.

A solution of ethidium bromide in pH 12.1 denaturation buffer is next prepared by adding 0.1 ml. of an ethidium bromide solution (22 $\mu$g ethidium bromide per ml. of 12.1 denaturation buffer) to 0.9 ml. of pH 12.1 denaturation buffer. A suitable denaturation buffer comprises 0.09 M $Na_3PO_4$: 0.01 M EDTA: 0.01 M NaCl, adjusted to pH 12.1 with 0.15 M NaOH. To 1 ml. of this ethidium bromide solution, there is added an aliquot (e.g. 100 $\mu$l) of this incubated serum mixture prepared above.

Fluorescence of the ethidium bromide: PM-2 DNA mixture is determined by a spectrophotofluorometer at 530 nm excitation and 590 nm emission. Fluorescence greater than background is caused by ethidium bromide binding to PM-2 DNA, so a change in fluorescence relative to a control reaction (identical to test sample except containing no bleomycin) allows the degree of bleomycin-induced degradation of PM-2 DNA to be quantified. From the fluorescence values, the percent inhibition of PM-2 DNA degradation caused by the presence of inhibitor presence X in the serum can easily be determined.

The concentration of inhibitor protein X in the serum sample is next determined by the conventional Lowry (folin phenol reagent) method as described in *J. Biol. Chem.* 193:265–275 (1951).

By plotting the percent inhibition of PM-2 DNA degradation against the log of the concentration of inhibitor protein X, the $IC_{50}$ value for the particular serum sample may be readily determined.

Once the $IC_{50}$ value for a given patient has been calculated, this value may be used directly to predict the probability of cancer in such patient. Extensive studies on healthy (cancer-free) patients and patients having a wide variety of malignant neoplasms have shown that inhibitor protein X is found in significantly lower amounts in the serum of patients having cancer. The $IC_{50}$ value, therefore, for cancer patients is found to be significantly elevated relative to the norm value for healthy individuals. This clear differentiation in $IC_{50}$ values provides a simple and accurate basis for detecting the presence of cancer and is the heart of the present invention.

The precise $IC_{50}$ value obtained from blood samples of cancer-free patients will vary to some degree with the particular individual. In patients tested to date, the mean $IC_{50}$ value for cancer-free patients has been found to be 90.2±11.0 $\mu$g/ml. (significant at the 0.001 level). The highest $IC_{50}$ value recorded for a healthy patient has been 120 $\mu$g/ml.

In cancer patients, the $IC_{50}$ values obtained varied with the type of cancer involved, but in all cases to date the value has been significantly higher than those obtained from cancer-free individuals. The lowest $IC_{50}$ value for a cancer patient to date has been 270 $\mu$g/ml. In general, however, an $IC_{50}$ value over about 200 indicates a high probability that the patient has a malignant neoplasm of some type.

The method of the present invention has been used successfully to detect a wide variety of cancer types and is thus believed to be generally applicable to cancer diagnosis. As specific examples of tumor types detected, there may be mentioned testicular carcinoma, lymphoma, leukemia, adenocarcinoma of the breast, small cell adenocarcinoma of the lung, large cell adenocarcinoma of the lung, adenocarcinoma of the colon and melanoma, to name just a few. The method also appears to be specific for cancer diagnosis since cancer-free patients having various types of non-neoplastic disease have not had the elevated $IC_{50}$ values associated with the presence of cancer.

The above-described fluorescence assay for inhibitor protein X of the present invention is based on an intrinsic property of this substance: inhibition of bleomycin induced degradation of PM-2 DNA. Serum levels of the protein determined by this method have been correlated with the presence or absence of malignant disease in the present invention. The availability of a purified inhibitor protein X permits a diversity of other methods known in the arts of biochemistry and clinical chemistry to be used for its measurement. Prominent among these are immunological methods such as radioimmunoassay, fluoroimmunoassay, enzyme immunoassay (e.g. ELISA), spin immunoassay, chemiluminescent immunoassay, fluorescence polarization immunoassay, nephelometricassay, gel diffusion methods and classical methods like hemagglutination and complement fixation. Furthermore, other functional properties of inhibitor protein X can be exploited for its measurement in biological fluids. Catalytic phenomena associated with the molecule can be measured in spectrophotometric or spectrofluorometric kinetic or end point assays. Additionally, separation technology can be applied to the fluid in question, and a variety of detection methods can be employed to quantitate the protein, including spectral or densitometric methods and immunological methods. Since specific measurement of inhibitor protein X concentration is obtained by the preceding methods, it follows that serum levels of the protein determined by such methods correlate with the presence or absence of malignant disease.

Inhibitor protein X was purified according to the following procedures.

Partial Purification—Procedure A

Inhibitor protein X was partially purified by Sephadex column chromatography. Human serum (1 ml.) was applied to a Sephadex G-75 column (88 cm. ×2 cm.) and then eluted in a sodium phosphate buffer (0.07 M, pH 6.8) at a flow rate of 6-8 ml. per hour at room temperature. The inhibitor was contained in the void volume which was pooled, lyophilized resuspended in 1 ml. $H_2O$, dialyzed against 20 volumes of $H_2O$ for 24 hours at 4° C., and then applied to a Sephadex G-200 column equilibrated in the same buffer.

Elution of the Sephadex G-200 column resulted in three peaks which absorbed at 280 nm. Peak III which accounted for 7.7% of the total protein eluted contained inhibitor protein X. This was treated as described above and then reapplied to a Sephadex G-200 column. Elution was effected with the phosphate buffer described above. Fractions (3 ml.) from each column were collected with a fraction collector (Gilson Medical Electronics, Inc., Middleton, Wis), and the elution patterns were obtained by measuring the absorbance at 280 nm with a spectrophotometer. Protein concentrations were determined by the Lowry method.

Purification—Procedure B

Purification of the inhibitor protein was achieved by molecular filtration with Amicon filters, dialysis and Sephadex gel column chromatography. The human sera (1-5 ml.) were centrifuged in Amicon Conical filter tubes (Amicon, Lexington, Mass.) at 5000 g. for 10 minutes at 4° C. The retentate that remained in the filter cone after the centrifugation was resuspended in deionized water to the original volume of sera. Aliquots of the retentate and the filtrate were tested for inhibitory activity. The active retentate was dialyzed in cellulose tubing agent 20 volumes of deionized water at 4° C. for 24 hours. The retentate and dialyzate were lyophilized and resuspended in deionized water. The results of assays of the two fractions showed the inhibitory activity was in the retentate. The retentate (1 ml.) was applied on a 60×5 cm. column of Sephadex G-50 and eluted with a sodium phosphate buffer (0.07 M, pH 6.8) at a flow rate of 30 ml. per hour at 4° C. The column eluate (5 ml. per tube) was collected with a Buchler Fractomette Alpha 200 (Searle, Fort Lee, N.J.) fraction collector. The 280 nm absorbance of each fraction was measured with a spectrophotometer and the tubes were pooled according to the absorbence peaks. The pooled fractions were lyophilized, dialyzed and tested for inhibitory activity as described above. The "active" material contained in the void volume fraction was applied of Sephadex G-75 and G-100 columns and eluted similarly to the G-50 column. The inhibitory activity was found in the void volume fractions of both columns. The "active" material that had been collected in the void volume fraction of the Sephadex G-200 column was eluted with sodium phosphate buffer (0.07 M, pH 6.8) at room temperature at a flow rate of 6-8 ml. per hour. The fractions were collected (3 ml. per tube) with a Gilson microfraction collector (Gilson, Middleton, Wis.). The column eluate was fractionated on the basis of the 280 nm absorbance profile by pooling the tubes under each peak of absorbence. Each fraction was then lyophilized, dialyzed and tested for inhibitory activity as described above. The inhibitory activity was found in fraction III. The material in fraction III was reapplied on the Sephadex G-200 column and eluted under the same conditions. The fraction III of the Sephadex G-200 column containing inhibitor protein X represented a greater than 1000-fold purification.

The PM-2 DNA fluorescence assay procedure for inhibitor protein X is described in more detail below:

Determination of $IC_{50}$ for Inhibitor Protein X

The determination of the $IC_{50}$ (the concentration of protein required to give 50 percent inhibition of PM-2 DNA degradation) for inhibitor protein X in human sera is performed in two steps:

1. The protein concentration in the serum is determined by the Lowry method.
2. The use of the PM-2 DNA fluorescence assay for bleomycin to obtain a dose-response curve for the serum protein inhibitor. The $IC_{50}$ values are derived from plots of percent inhibition of DNA degradation versus the protein concentrations done onlog-probit graphs.

Procedures

I. Lowry Reaction
A. Preparation of stock solutions:
Solution A. 2% $Na_2CO_3$ in 0.1 N NaOH
Solution B. 1% $CuSO_4.5H_2O$ in $H_2O$.
Solution C. 2% Na+K+ tartrate in $H_2O$.
Solution D. 2N Folin-Ciocalteau Phenol Reagent
B. Preparation of reagent solutions
Reagent Solution 1. Mix 1 volume of Stock Solution B with 1 volume of Stock Solution C.
Reagent Solution 2. Mix 50 volumes of Stock Solution A with 1 volume of Reagent Solution 1
Reagent Solution 3. Mix 1 volume Stock Solution D with 1 volume of $H_2O$.
C. Reactions
1. Dilute the sera 1:10 with $H_2O$.
2. Transfer 10 μl of diluted sera to a 13×100 mm glass test tube and add 290 μl $H_2O$.
3. Add 1 ml of Reagent Solution 2, mix well, and incubate 10 minutes at room temperature.
4. Add 100 μl of Reagent Solution 3, mix well, and incubate 30 minutes at room temperature.
5. Use a spectrophotometer to measure the absorbance at 750 nm.
6. Determine the protein concentration from the BSA Standard curve.
D. Bovine Serum Albumin (BSA) Standard Curve
1. Prepare serial dilutions of BSA (eg. 25, 50, 75, 100, 150 μg/ml) in a final volume of 0.3 ml.
2. Perform the reactions given in Section C starting at Step C (addition of Reagent Solution 2).
3. Plot the absorbance at 750 nm versus BSA concentrations.
II. The Protein Inhibitor Assay
A. Perform serial dilutions of the serum protein, on the basis of the serum protein concentrations determined by the Lowry Reaction. Make the dilutions in a constant volume of sodium borate buffer (0.05 M, pH 9.5).

B. Add the samples of serum protein (50 μl volume) to 10 μl of bleomycin (34.5 nanamoles) contained in a glass test tube (13×100 mm).

C. Add 390 μl of sodium borate buffer (0.05 M, pH 9.5) containing 25 mM 2-mercaptoethanol.

D. Add 50 μl of PM-2 DNA ($8.3 \times 10^{-6}$ M in 0.15 M NaCl)

E. Incubate 30 minutes at 37° C.

F. Transfer triplicate aliquots (100 μl) to glass test tubes (13×100 mm) containing 0.9 ml $Na_3PO_4$ (0.09 M, pH 12.1) containing 0.01 M EDTA and 0.01 M NaCl. Mix well.

G. Add 100 μl of ethidium bromide ($55.7 \times 10^{-6}$ M) in the $Na_3PO_4$ buffer, Ph 12.1. Mix well.

H. Controls:
1. Sodium borate (0.5 M, pH 9.5) containing 2-mercaptoethanol without bleomycin or proteins.
2. Protein without bleomycin or PM-2 DNA.
3. Protein without bleomycin.
4. Sodium borate (0.05 M pH 9.5) containing 2-mercaptoethanol blank sample.

I. Spectrophotofluorometry (Aminco-Bowman)

Transfer the sample of 1 cm quartz cuvette and measure the fluoroscence at 530 nm excitation and 590 emission.

We claim:

1. A method for detecting cancer in humans which comprises the steps of
   (a) obtaining a blood sample from a patient to be screened for cancer;
   (b) determining the concentration of inhibitor protein X in said sample; and
   (c) comparing said concentration as determined in step (b) with the norm inhibitor protein X concentration associated with serum of cancer-free patients, whereby a significant reduction of inhibitor protein X concentration relative to the norm concentration indicates the probability of cancer.

2. A method for detecting cancer in humans which comprises the steps of
   (a) obtaining a blood sample from a patient to be screened for cancer;
   (b) determining the concentration of inhibitor protein X in said sample required to inhibit 50% of bleomycin-induced degradation of PM-2 DNA; and
   (c) comparing said $IC_{50}$ value as determined in step (b) with the norm $IC_{50}$ value associated with serum of cancer-free patients, whereby a significant elevation of said $IC_{50}$ value from the norm value indicates the probability of cancer.

3. The method according to claim 2 wherein determination of the $IC_{50}$ value in step (b) is made by the steps of
   (1) preparing a mixture of the blood sample with a solution of bleomycin, PM-2 DNA and 2-mercaptoethanol in pH 9.5 buffer;
   (2) incubating the mixture from step (1) for 30 minutes as a temperature of 37° C.;
   (3) adding an aliquot of the mixture from step (2) to a mixture of ethidium bromide in a pH 12.1 denaturation buffer;
   (4) determining the fluoroescence of the ethidium bromide: PM-2 DNA mixture from step (3) with a spectrophotofluorometer at 530 nm excitation and 590 nm emission;
   (5) determining the percent inhibition of bleomycin-induced PM-2 DNA degradation from the change in fluorescence of the sample relative to a control sample containing no bleomycin:
   (6) determining the concentration of inhibitor protein X by the Lowry method; and
   (7) determining from the values obtained in steps (5) and (6) the concentration of inhibitor protein X required to inhibit 50% of bleomycin-induced PM-2 DNA degradation.

* * * * *